(12) United States Patent
Lesko

(10) Patent No.: US 7,540,840 B2
(45) Date of Patent: Jun. 2, 2009

(54) ILLUMINABLE TONGUE DEPRESSOR ASSEMBLY

(76) Inventor: Robert Lesko, 104 Twin Cedar Ct., Ponte Vedra Beach, FL (US) 32082

( * ) Notice: Subject to any disclaimer, the term of this patent is extended or adjusted under 35 U.S.C. 154(b) by 512 days.

(21) Appl. No.: 11/220,469

(22) Filed: Sep. 8, 2005

(65) Prior Publication Data
US 2007/0055112 A1 Mar. 8, 2007

(51) Int. Cl.
*A61B 1/32* (2006.01)
(52) U.S. Cl. ...................................... 600/241
(58) Field of Classification Search ................. 600/235, 600/237, 240, 241, 223, 248; 206/63.5, 380, 206/438, 514
See application file for complete search history.

(56) References Cited
U.S. PATENT DOCUMENTS 2,735,778 A * 2/1956 Taylor ......................... 426/110
4,501,363 A * 2/1985 Isbey, Jr. ..................... 206/570
4,643,172 A * 2/1987 Taff et al. .................... 600/203
4,807,599 A * 2/1989 Robinson et al. ............ 600/212

* cited by examiner

*Primary Examiner*—Eduardo C Robert
*Assistant Examiner*—Elana B Fisher

(57) ABSTRACT

A tongue depressor includes a handle that can be grasped and held within a user's hand. An elongated implement is connected to a distal end of the handle and protrudes forwardly therefrom. A light source is situated to an interior of the handle and is proximally adjoined to the implement. The light source faces outwardly from the handle and emits light along a length of the implement. A power supply source is coupled to the light source. The light source is adaptable between on and off modes. A base member includes a grooved portion extending through a top surface thereof that receives and stores the handle therein. A recessed depression is formed adjacent to the grooved portion. A rack is positional into the recessed depression and is provided with notches that receive and support new implements therein.

7 Claims, 10 Drawing Sheets

ILLUMINABLE TONGUE DEPRESSOR ASSEMBLY

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to tongue depressors and, more particularly, to an illuminable tongue depressor assembly for illuminating a confined target zone during medical procedures and the like.

2. Prior Art

Tongue depressors have been in use routinely in the examination of patients for a very long time. Despite efforts to develop and manufacture tongue depressors of other materials, by far the most commonly used tongue depressors are those constructed of wood. Suggestions have been made for substituting a synthetic resin material for wood, but wood is still the preferred material, and large numbers of wooden tongue depressors are consumed annually. One suggestion for supplanting the wooden tongue depressor with a more effective diagnostic aid is a luminous spatula in which a spatula of light-conductive material is illuminated by a light source to assist in the examination of a patient.

One such an example is disclosed in the prior art, in which a light-conductive spatula is associated with a torch for receiving light from a lamp in the torch. The spatula includes a beaded stiffening configuration. A luminous head on the spatula is provided with a top surface configuration which enables light to be refracted over the whole area of the top surface, as well as from the edges, for illumination of the cavity being examined. Unfortunately, this example provides no illumination along the bottom surface, thus requiring the user to turn it over for illuminating surface located beneath the spatula. This is time consuming and might lead to injuries as the person manipulating the spatula can inadvertently scrape the interior of the examinee's mouth.

Accordingly, a need remains for an illuminable tongue depressor assembly in order to overcome the above-noted shortcomings. The present invention satisfies such a need by providing an illuminable tongue depressor that is safe and easy to use and allows for more complete and expedient oral examinations. Such an illuminable tongue depressor advantageously allows medical examiners to better visualize the interior of a patient's oral cavity, which in turn can lead to an improved and more correct diagnosis.

BRIEF SUMMARY OF THE INVENTION

In view of the foregoing background, it is therefore an object of the present invention to provide an illuminable tongue depressor assembly. These and other objects, features, and advantages of the invention are provided by a tongue depressor for conveniently illuminating a confined target zone during medical procedures and the like.

The tongue depressor includes a handle section that is suitably sized and shaped for conveniently being grasped and held within a user's hand. An elongated implement is connected to a distal end portion of the handle section and protrudes forwardly therefrom. Such an implement has a longitudinal axis centrally registered with a longitudinal length of the handle section. The implement may include a central shaft that has a concave shape and an arcuate distal end portion provided with a plurality of laterally offset ribs equidistantly stepped away from the proximal end portion. A shield is directly conjoined to the central shaft and disposed adjacent to the proximal end portion thereof. Such a shield lays contiguous with the central shaft and is suitably sized and shaped for advantageously and effectively preventing the central shaft from moving beyond a predetermined location within the handle section.

The implement preferably further includes a notch formed in the proximal end portion thereof. Such a notch is removably engageable directly with an outer wall of the casing such that the implement is effectively held at a tensed position and statically abutted against the casing during operating conditions. The implement is slidably ejected from the handle section when the push button is laterally biased towards the axis thereby causing the casing outer wall to disengage from the implement notch while linearly and laterally traversing through the handle section.

A light-emitting source is situated to an interior of the handle section and is proximally adjoined to the implement. Such a light-emitting source faces outwardly from the handle section and emits a light ray linearly along a longitudinal length of the implement in such a manner that the target zone and the implement are advantageously simultaneously illuminated during operating conditions. A power supply source is electrically coupled to the light-emitting source. Such a light-emitting source is conveniently and selectively adaptable between on and off modes as desired by the user.

The light-emitting source preferably includes an LED driver seated within the handle section and electrically mated to the power supply source. At least one LED is electrically mated to the LED driver and disposed rearward of the casing. Such an LED is centrally aligned along the axis wherein the light ray travels linearly along a longitudinal length of the implement. A control button is directly abutted against a top surface of the handle section and operably engaged with the LED driver.

A base member includes a grooved portion extending downwardly through a top surface thereof. Such a grooved portion is suitably sized and shaped for conveniently receiving and storing the handle section therein during non-operating conditions. The base member further includes a recessed depression formed adjacent to the grooved portion. Such a base member also includes a rack removably positional directly into the recessed depression. The rack is provided with a plurality equidistantly spaced notches formed therein. Each notch is suitably sized and shaped for effectively receiving and supporting a new one of the implements therein such that the user can advantageously selectively withdraw the new implements as needed during operating conditions.

The assembly preferably further includes a mechanism for selectively ejecting the implement from the handle section such that the implement can conveniently be discarded after a single use. Such an ejecting mechanism includes a push button directly traversing through a side of the handle section and is adaptable between engaged and disengaged positions defined along a travel path registered orthogonal to the axis.

The control and push buttons may be spaced along adjacent surfaces of the handle section such that the user can advantageously simultaneously depress the control and push buttons with alternate fingers while holding the handle section with one hand.

A casing including top and bottom sides is provided with a monolithically formed lip portion oppositely spaced thereal-ong and flanging away from a center of the casing. Such a casing has a central opening formed therein. The opening is suitably sized and shaped wherein a proximal end portion of the implement is slidably intercalated therethrough and is spaced from the control button. The lip portions are directly abutted against an interior surface of the handle section for advantageously and effectively prohibiting the casing from laterally displacing beyond a predetermined linear path. A resilient spring member has a first arm directly positioned through the casing and maintains a fixed spatial relationship therewith during operating conditions. Such a spring member may further have a second arm oppositely situated from the first arm and directly anchored to a distal end portion of the handle section. The second arm remains stationary while the first arm is biased along a linear path when the push button is depressed during ejection procedures.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
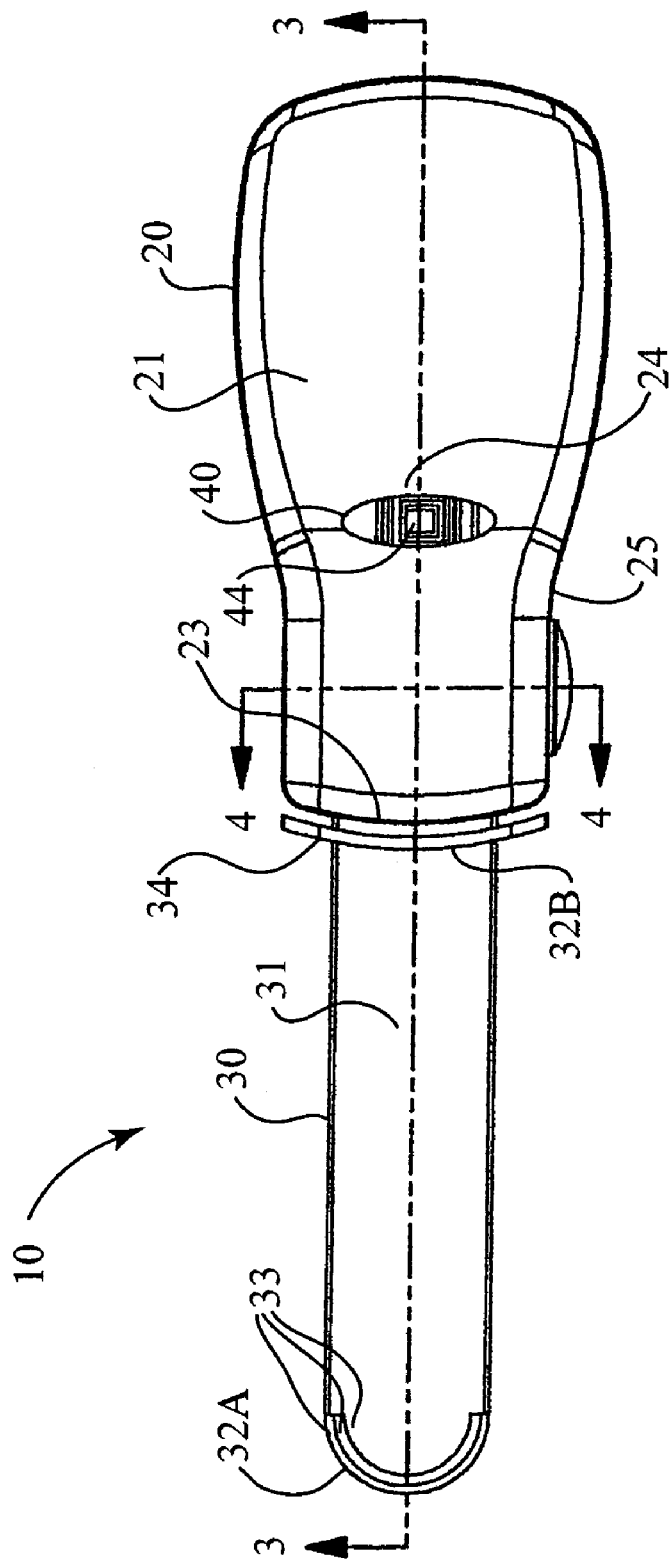
FIG. 1 is a top plan view showing an illuminable tongue depressor assembly, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The assembly of this invention is referred to generally in FIGS. 1-18 by the reference numeral 10 and is intended to provide an illuminable tongue depressor assembly. It should be understood that the assembly 10 may be used for many different types of examinations and should not be limited in use to only medical and/or oral examinations.

Figure 2:
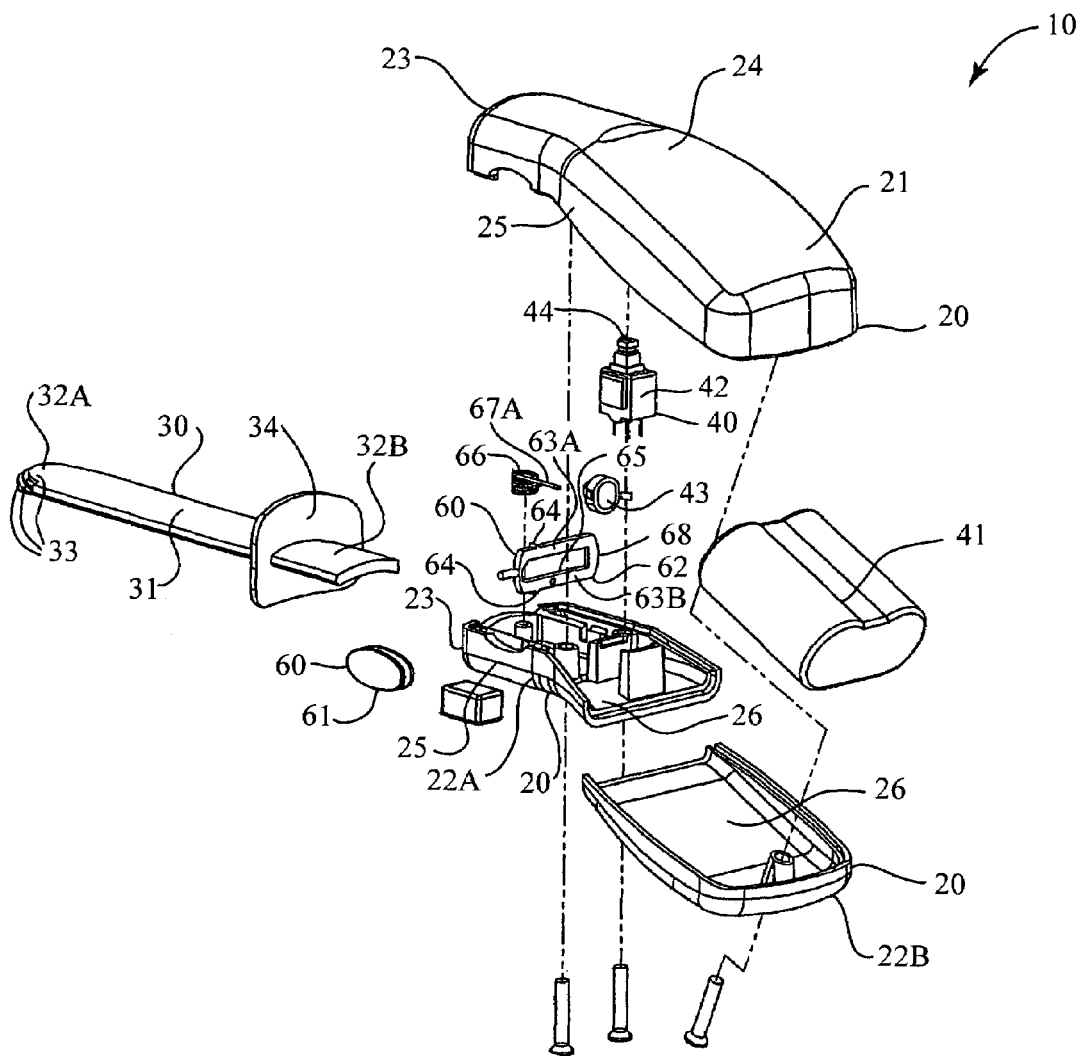
FIG. 2 is an exploded perspective view of the assembly shown in FIG. 1.
Figure 12:
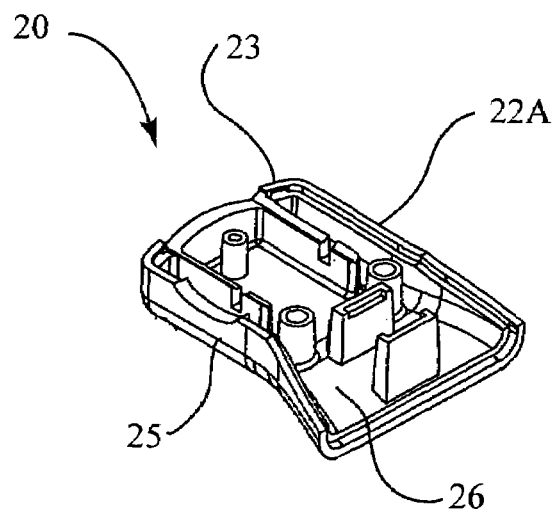
FIG. 12 is a perspective view of the first bottom portion of the handle section shown in FIG. 2.
Figure 13:
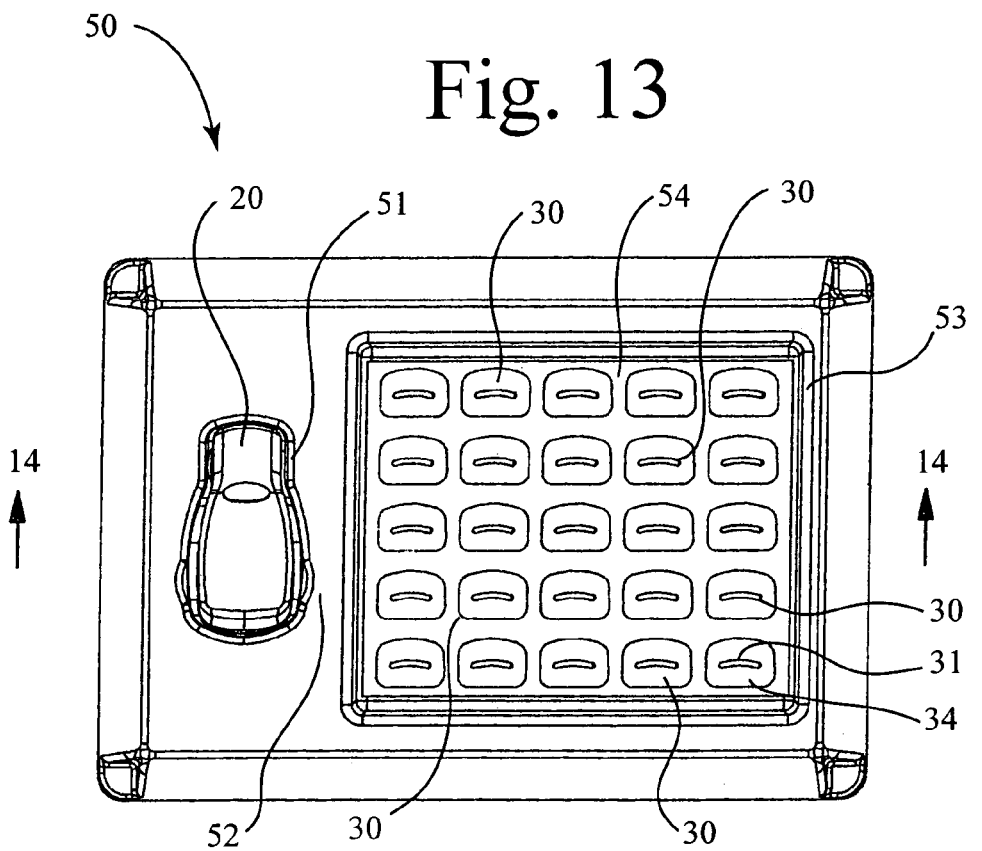
FIG. 13 is a top plan view of the base member, in accordance with the present invention.
Figure 14:
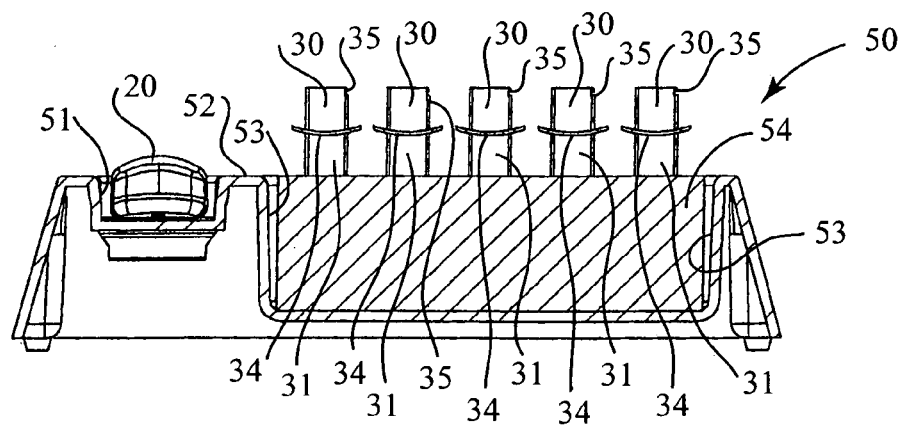
FIG. 14 is a cross-sectional view of the base member shown in FIG. 12, taken along line 14-14.
Figure 15:
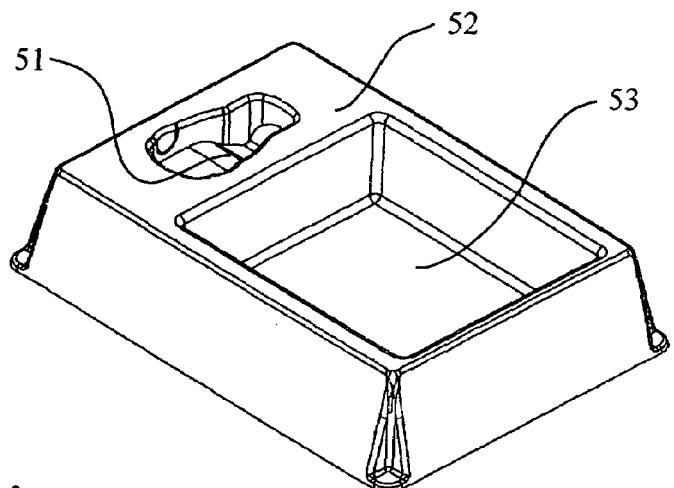
FIG. 15 is a perspective view of the base member shown in FIG. 13, without the rack positioned therein.
Figure 16:
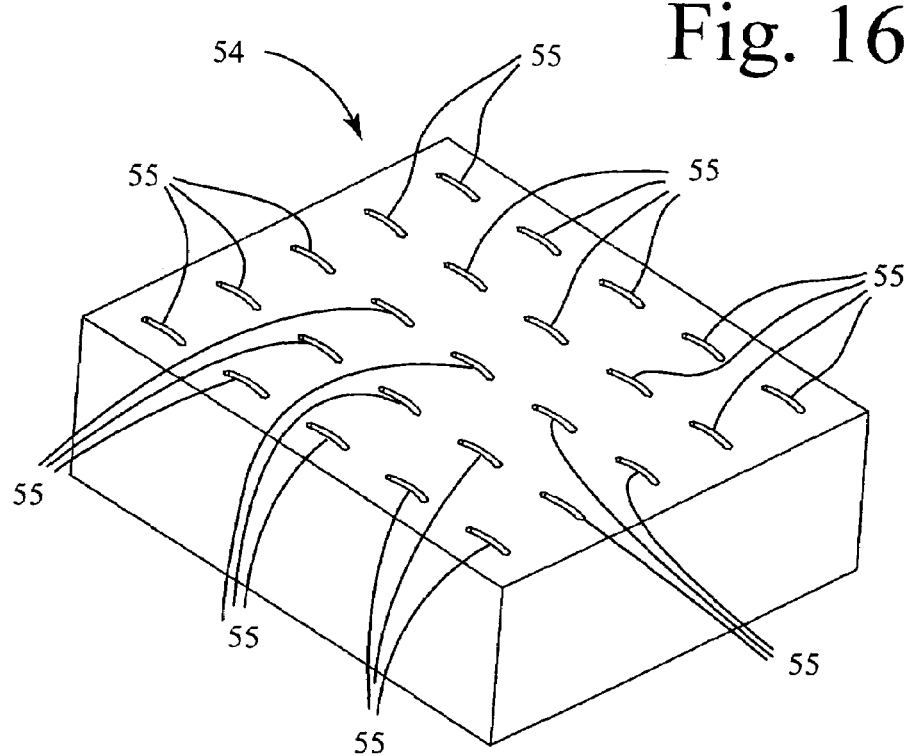
FIG. 16 is a perspective view of the rack shown in FIG. 13.
Figure 17:
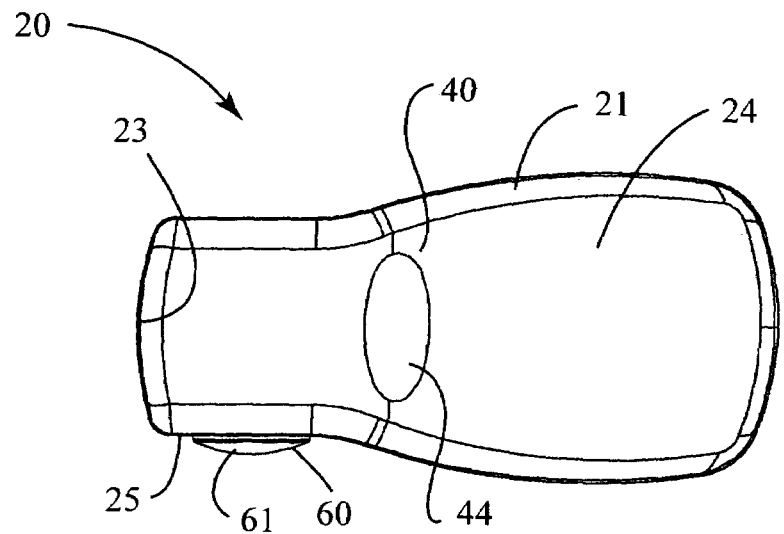
FIG. 17 is a top-plan view of the handle section show in FIG. 1.
Figure 18:
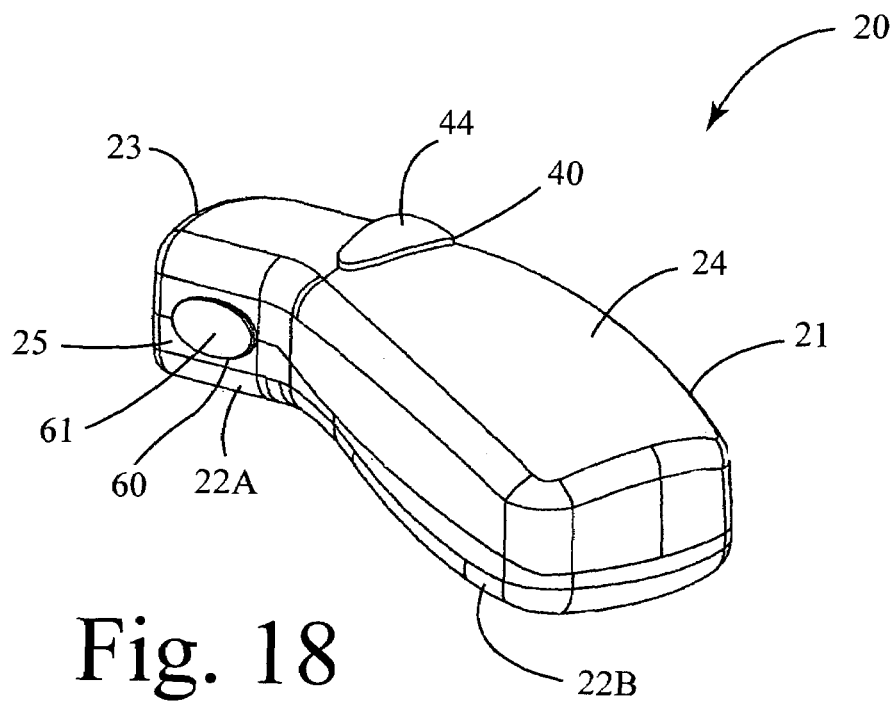
FIG. 18 is a perspective view of the handle section shown in FIG. 17.

Referring initially to FIGS. 1 through 5, 12 through 14, and 17 and 18, the assembly 10 includes a handle section 20 that is suitably sized and shaped for conveniently being grasped and held within a user's hand. Such a handle section 20 includes removably and directly connected, without the use of intervening elements, upper 21 and lower 22 portions. The lower portion 22 further includes first 22A and second 22B sections, as is best shown in FIGS. 2 and 12.

Referring to FIG. 1 through 10, and 13 and 14, an elongated implement 30 is connected to a distal end portion 23 of the handle section 20 and protrudes forwardly therefrom. Such an implement 30 may be formed from disposable and recycled material commonly employed in the medical industry and readily obvious to a person of ordinary skill in the art of medical equipment. Implement 30 has a longitudinal axis centrally registered with a longitudinal length of the handle section 20. The implement 30 includes a central shaft 31 that has a concave shape and an arcuate distal end portion 32A provided with a plurality of laterally offset ribs 33 equidistantly stepped away from the proximal end portion 32B. Of course, the shaft 31 may be produced in a variety of different shapes depending on the required use thereof, as is obvious to a person of ordinary skill in the art. The offset ribs 33 can conveniently be used by the examiner to remove debris or epithelial cell samples, for testing, from the patient's mouth.

A shield 34 is directly conjoined, without the use of intervening elements, to the central shaft 31 and disposed adjacent to the proximal end portion 32B thereof. Such a shield 34 lays contiguous with the central shaft 31 and is suitably sized and shaped for advantageously and effectively preventing the central shaft 31 from moving beyond a predetermined location within the handle section 20. The shield 34 also prevents the implement 30 from being inserted beyond a comfortable distance into the patient's mouth, which often occurs with conventional tongue depressors and leads to an inconvenient reflex of the esophagus, commonly known as a "gag" reflex.

Referring to FIGS. 4, 6, 10 and 14, the implement 30 further includes a notch 35 formed in the proximal end portion 32B thereof. Such a notch 35 is removably engageable directly, without the use of intervening elements, with an outer wall 68 of the casing 62 (described herein below), which is essential such that the implement 30 is effectively held at a tensed position and statically abutted against the casing 62 during operating conditions. The implement 30 is slidably ejected from the handle section 20 when the push button 61 (described herein below) is laterally biased towards the axis thereby causing the casing outer wall 68 to disengage from the implement notch 35 while linearly and laterally traversing through the handle section 20. This feature advantageously eliminates the need for the examiner to manually remove the implement 30, which may have become contaminated with contagious agents during the examination, thus increasing the safety and sanitation of the examiner and the examination process, respectively.

Figure 3:
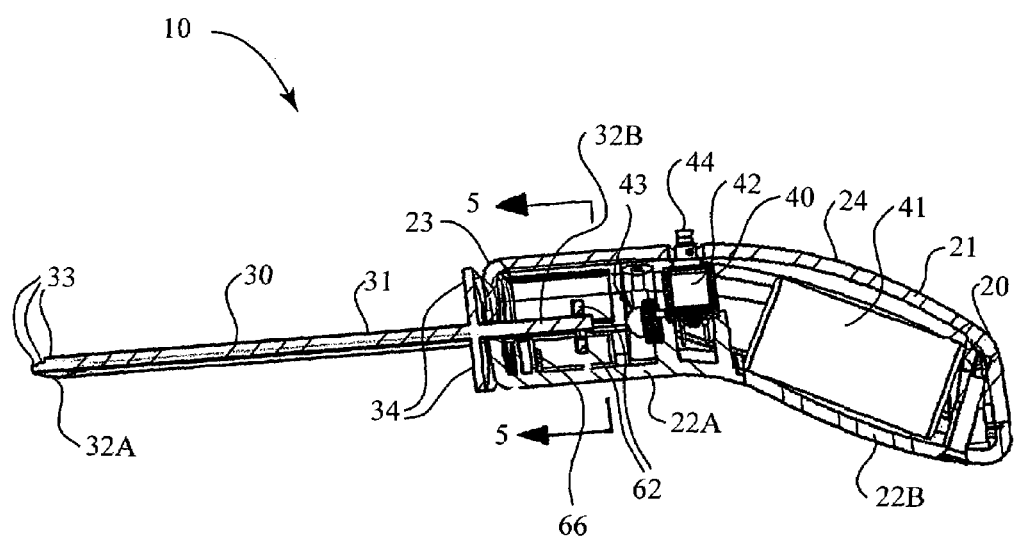
FIG. 3 is a cross-sectional view of the assembly shown in FIG. 1, taken along line 3-3.
Figure 4:
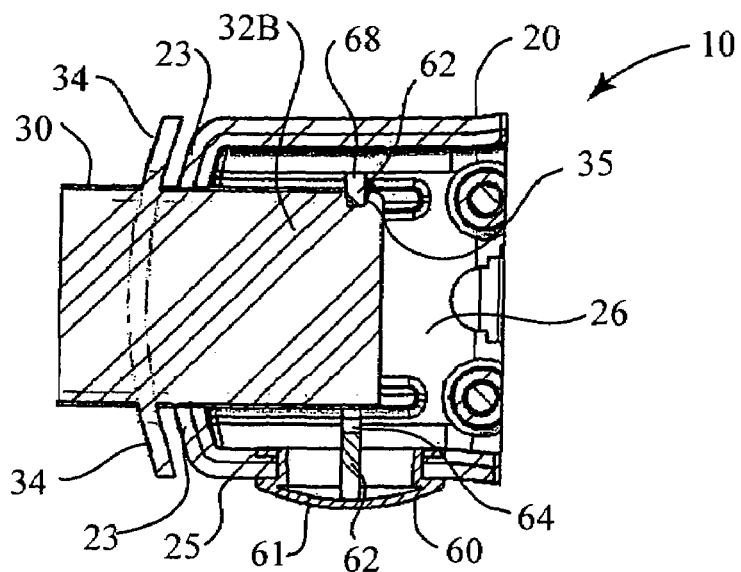
FIG. 4 is a cross-sectional view of the handle section shown in FIG. 1, taken along line 44.
Figure 5:
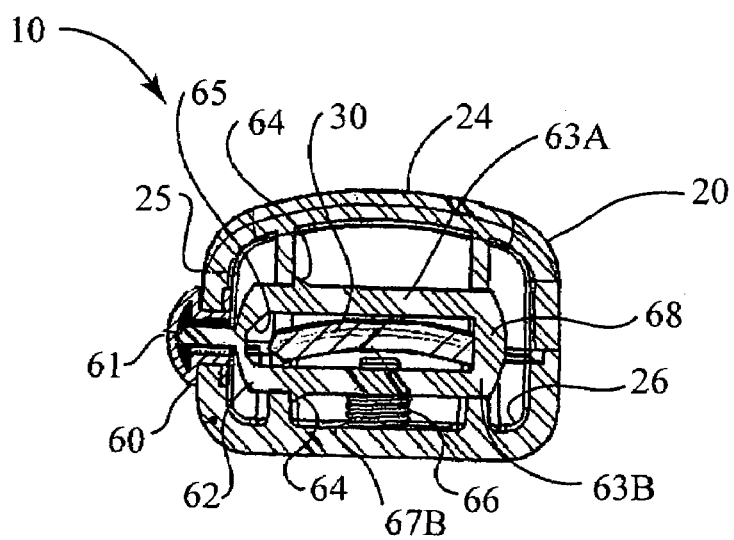
FIG. 5 is a cross-sectional view of the handle section shown in FIG. 4, taken along line 5-5.
Figure 7:
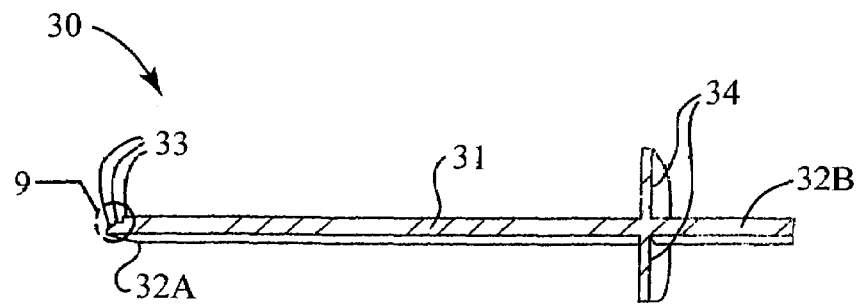
FIG. 7 is a cross-sectional view of the elongated implement shown in FIG. 6, taken along line 7-7.
Figure 6:
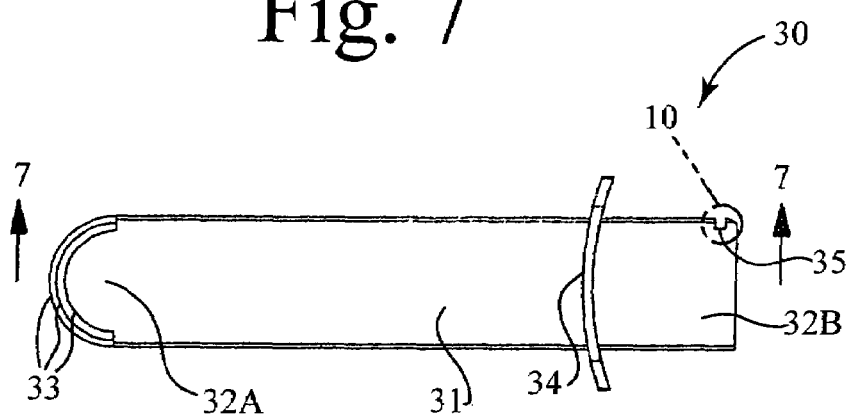
FIG. 6 is a top plan view of the elongated implement shown in FIG. 1.
Figure 8:
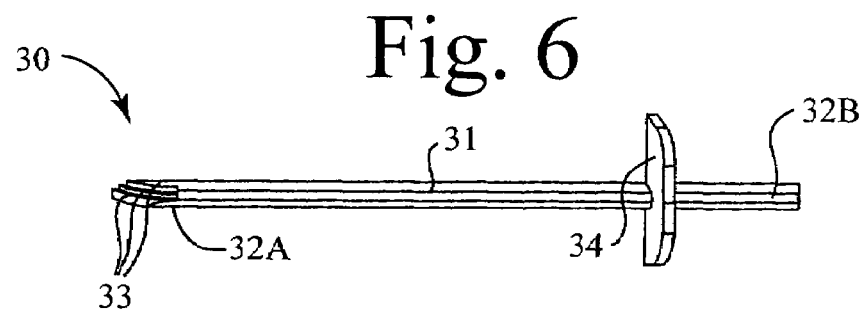
FIG. 8 is a side-elevational view of the elongated implement shown in FIG. 6.
Figure 9:
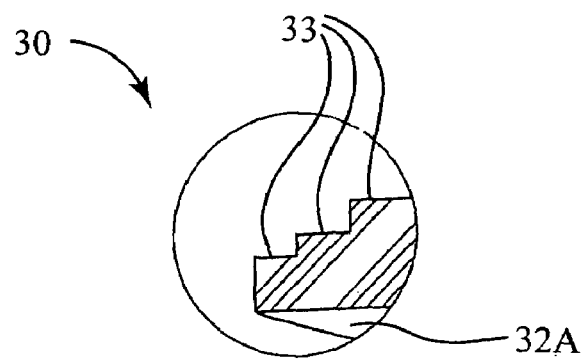
FIG. 9 is an enlarged view of section 9 shown in FIG. 7, showing the plurality of off-set ribs.
Figure 10:
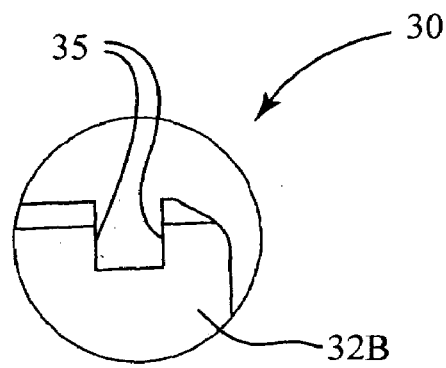
FIG. 10 is an enlarged view of section 10 shown in FIG. 6, showing the notch formed in the proximal end portion.
Figure 11:
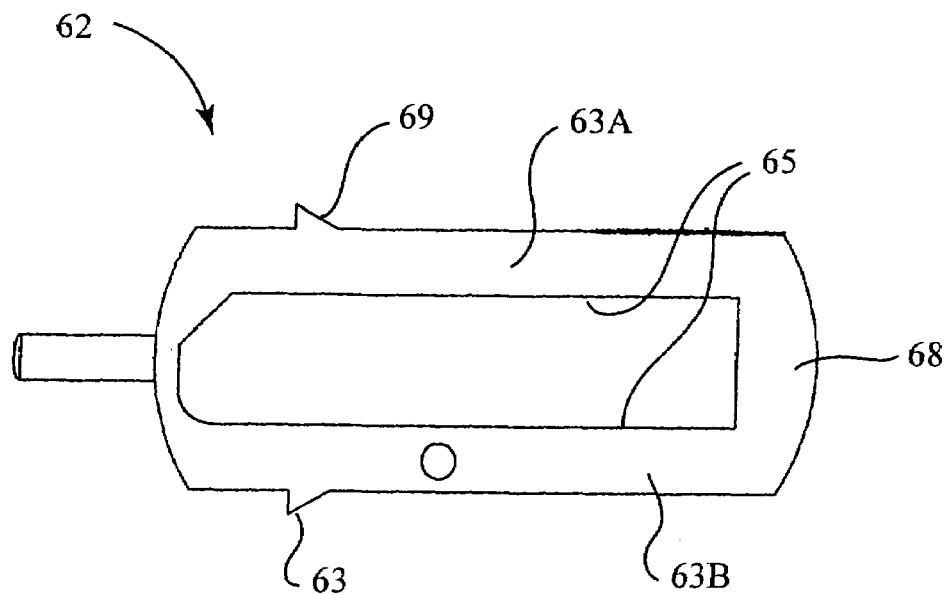
FIG. 11 is a front-elevational view of the casing shown in FIG. 2.

Referring to FIGS. 2, 3 and 4, a light-emitting source 40 is situated to an interior of the handle section 20 and is proximally adjoined to the implement 30. Such a light-emitting source 40 faces outwardly from the handle section 20, which is a vital feature for allowing same to emit a light ray linearly along a longitudinal length of the implement 30 in such a manner that the target zone and the implement 30 are advantageously simultaneously illuminated during operating conditions. This allows the examiner to more clearly see the target zone, while also allowing for better manipulation of the implement 30 within the examinee's mouth, thus reducing the risk of causing inadvertent injuries with the implement 30. A power supply source 41 is electrically coupled to the light-emitting source 40. Such a light-emitting source 40 is conveniently and selectively adaptable between on and off modes as desired by the user, thus allowing a user to conserve the power supply source 41, which in turn increases the effective periods of use of the assembly 10.

Still referring to FIGS. 2, 3 and 4, the light-emitting source 40 includes an LED driver 42 seated within the handle section 20 and electrically mated to the power supply source 41. At least one LED 43 is electrically mated to the LED driver 42 and disposed rearward of the casing. Such an LED 43 is centrally aligned along the axis wherein the light ray travels linearly along a longitudinal length of the implement 30. In preferred embodiment, LED driver 42 may be purchased from www.LEDSupply.com. Such a vendor sells a 2-cell 1 W MicroPuck LED driver, soldered with a white Luxeon 1 Star LED suitable for the present invention. Such a LED and associated driver provide an efficient and stable illumination while mimicking the light drop-off of a conventional incandescent bulb, which dims as the batteries are used up. The driver is advantageously insulated by an epoxy and is resistant to harsh environments and moisture commonly encountered in the medical field. A control button 44 is directly abutted, without the use of intervening elements, against a top surface 24 of the handle section 20 and operably engaged with the LED driver 42.

Referring to FIGS. 13, 14, 15 and 16, a base member 50 includes a grooved portion 51 extending downwardly through a top surface 52 thereof. Such a grooved portion 51 is suitably sized and shaped for conveniently receiving and storing the handle section 20 therein during non-operating conditions, as is best shown on FIGS. 13 and 14. The base member 50 further includes a recessed depression 53 formed adjacent to the grooved portion 51. Such a base member 50 also includes a rack 54 removably positional directly into the recessed depression 53, without the use of intervening elements. The rack 54 is provided with a plurality equidistantly spaced notches 55 formed therein. Each notch 55 is suitably sized and shaped for effectively receiving and supporting a new one of the implements 30 therein, which is critical and convenient such that the user can advantageously selectively withdraw the new implements 30 as needed during operating conditions.

Referring to FIGS. 1 through 5, 11, 17 and 18, the assembly 10 further includes a mechanism 60 for selectively ejecting the implement 30 from the handle section 20, which is crucial and advantageous such that the implement 30 can conveniently be discarded after a single use, thus preventing the spread of disease from implements 30 that are re-used. Such an ejecting mechanism 60 includes a push button 61 directly traversing, without the use of intervening elements, through a side 25 of the handle section 20 and is adaptable between engaged and disengaged positions defined along a travel path registered orthogonal to the axis. The control 44 and push 61 buttons are spaced along adjacent surfaces of the handle section 20, which is vital and advantageous such that the user can simultaneously depress the control 44 and push 61 buttons with alternate fingers while holding the handle section 20 with one hand. Thus the examiner's other hand can be used to manipulate other tools or to take notes on what is seen during the examination.

Referring to FIGS. 2, 3, 4, 5 and 11, a casing 62 including top 63A and bottom 63B sides is provided with a monolithically formed lip portion 64 oppositely spaced therealong and flanging away from a center of the casing 62. Such a casing 62 has a central opening 65 formed therein. The opening 65 is suitably sized and shaped wherein a proximal end portion 32B of the implement 30 is slidably intercalated therethrough and is spaced from the control button 44. The lip portions 63 are directly abutted, without the use of intervening elements, against an interior surface 26 of the handle section 20, which is important for advantageously and effectively prohibiting the casing 62 from laterally displacing beyond a predetermined linear path. A resilient spring member 66 has a first arm 67A directly positioned, without the use of intervening elements, through the casing 62 and maintains a fixed spatial relationship therewith during operating conditions. Such a spring member 66 further has a second arm 67B oppositely situated from the first arm 67A and directly anchored, without the use of intervening elements, to a distal end portion 23 of the handle section 20. The second arm 67B remains stationary while the first arm 67A is biased along a linear path when the push button 61 is depressed during ejection procedures.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A tongue depressor for illuminating a confined target zone during medical procedures and the like, said tongue depressor comprising:
   a handle section suitably sized and shaped for being grasped and held within a user's hand;
   an elongated implement connected to a distal end portion of said handle section and protruding forwardly therefrom, said implement having a longitudinal axis centrally registered with a longitudinal length of said handle section;
   a light-emitting source situated interior of said handle section and proximally adjoined to said implement, said light-emitting source facing outwardly from said handle section and emitting a light ray linearly along a longitudinal length of said implement in such a manner that the target zone and said implement are simultaneously illuminated during operating conditions; and
   a power supply source electrically coupled to said light-emitting source, said light-emitting source being selectively adaptable between on and off modes as desired by the user;
   wherein said implement comprises a central shaft having a concave shape and an arcuate distal end portion provided with a plurality of laterally offset ribs equidistantly stepped away from said proximal end portion; and a shield directly conjoined to said central shaft and disposed adjacent said proximal end portion thereof, said shield laying contiguous with said central shaft and being suitably sized and shaped for preventing said central shaft from moving beyond a predetermined location within said handle section;
   wherein said shield is situated distal to said proximal end of said central shaft such that said shield remains positioned exterior of said handle section when said proximal end portion of said central shaft is inserted inside said handle section;
   means for selectively ejecting said implement from said handle section such that said implement can be discarded after a single use, said ejecting means comprising a push button directly traversing through a side of said handle section and being adaptable between engaged and disengaged positions defined along a travel path registered orthogonal to the longitudinal axis;
   a casing located within the handle section including top and bottom sides, each side provided with a monolithically formed lip portion, said lip portions being oppositely spaced along said top and bottom sides and flanging away from a center of said casing, said casing having a central opening formed therein, said opening being suitably sized and shaped wherein a proximal end portion of said implement is slidably intercalated therethrough, said lip portions being directly abutted against oppositely spaced interior surfaces of said handle section for prohibiting said casing from laterally displacing beyond a predetermined linear path, and
   a resilient spring member having a first arm directly positioned through said casing and maintaining a fixed spatial relationship therewith during operating conditions;
   wherein said implement includes a notch formed in said proximal end portion thereof, said notch being removably engageable directly with an outer wall of said casing such that said implement is held at a tensed position and statically abutted against said casing during operating conditions, said implement being slidably ejected from said handle section when said push button is laterally biased towards the longitudinal axis thereby causing said casing outer wall to disengage from said implement notch while linearly and laterally traversing through said handle section.

2. The assembly of claim 1, wherein said light-emitting source comprises:
   an LED driver seated within said handle section and electrically mated to said power supply source;
   at least one LED electrically mated to said LED driver and disposed rearward of said casing, said LED being centrally aligned along the axis wherein the light ray travels linearly along a longitudinal length of said implement; and
   a control button directly abutted against a top surface of said handle section and operably engaged with said LED driver.

3. The assembly of claim 2, wherein said control and push buttons are spaced along adjacent surfaces of said handle section such that the user can simultaneously depress said control and push buttons with alternate fingers while holding said handle section with one hand.

4. The assembly of claim 1, wherein said spring member further has a second arm oppositely situated from said first arm and directly anchored to a distal end portion of said handle section, said second arm remaining stationary while said first arm is biased along a linear path when said push button is depressed during ejection procedures.

5. A tongue depressor for illuminating a confined target zone during medical procedures and the like, said tongue depressor comprising:
   a handle section suitably sized and shaped for being grasped and held within a user's hand;
   an elongated implement connected to a distal end portion of said handle section and protruding forwardly therefrom, said implement having a longitudinal axis centrally registered with a longitudinal length of said handle section;
   a light-emitting source situated interior of said handle section and proximally adjoined to said implement, said light-emitting source facing outwardly from said handle section and emitting a light ray linearly along a longitudinal length of said implement in such a manner that the target zone and said implement are simultaneously illuminated during operating conditions; and
   a power supply source electrically coupled to said light-emitting source, said light-emitting source being selectively adaptable between on and off modes as desired by the user; and
   a base member including a grooved portion extending downwardly through a top surface thereof said grooved portion being suitably sized and shaped for receiving and storing said handle section therein during non-operating conditions, said base member further including a recessed depression formed adjacent said grooved portion;
   wherein said implement comprises a central shaft having a concave shape and an arcuate distal end portion provided with a plurality of laterally offset ribs equidistantly stepped away from said proximal end portion; and a shield directly conjoined to said central shaft and disposed adjacent said proximal end portion thereof said shield laying contiguous with said central shaft and being suitably sized and shaped for preventing said central shaft from moving beyond a predetermined location within said handle section;
   wherein said shield is situated distal to said proximal end of said central shaft such that said shield remains positioned exterior of said handle section when said proximal end portion of said central shaft is inserted inside said handle section;

means for selectively ejecting said implement from said handle section such that said implement can be discarded after a single use, said ejecting means comprising a push button directly traversing through a side of said handle section and being adaptable between engaged and disengaged positions defined along a travel path registered orthogonal to the longitudinal axis;

a casing located within the handle section including top and bottom sides, each side provided with a monolithically formed lip portion, said lip portions being oppositely spaced along said top and bottom sides and flanging away from a center of said casing, said casing having a central opening formed therein, said opening being suitably sized and shaped wherein a proximal end portion of said implement is slidably intercalated therethrough, said lip portions being directly abutted against oppositely spaced interior surfaces of said handle section for prohibiting said casing from laterally displacing beyond a predetermined linear path, and a resilient spring member having a first arm directly positioned through said casing and maintaining a fixed spatial relationship therewith during operating conditions;

wherein said implement includes a notch formed in said proximal end portion thereof, said notch being removably engageable directly with an outer wall of said casing such that said implement is held at a tensed position and statically abutted against said casing during operating conditions, said implement being slidably ejected from said handle section when said push button is laterally biased towards the longitudinal axis thereby causing said casing outer wall to disengage from said implement notch while linearly and laterally traversing through said handle section;

wherein said spring member further has a second arm oppositely situated from said first arm and directly anchored to a distal end portion of said handle section, said second arm remaining stationary while said first arm is biased along a linear path when said push button is depressed during ejection procedures.

6. The assembly of claim 5, wherein said light-emitting source comprises:

an LED driver seated within said handle section and electrically mated to said power supply source;

at least one LED electrically mated to said LED driver and disposed rearward of said casing, said LED being centrally aligned along the axis wherein the light ray travels linearly along a longitudinal length of said implement; and a control button directly abutted against a top surface of said handle section and operably engaged with said LED driver.

7. The assembly of claim 6, wherein said control and push buttons are spaced along adjacent surfaces of said handle section such that the user can simultaneously depress said control and push buttons with alternate fingers while holding said handle section with one hand.

* * * * *